United States Patent
Bredehöft et al.

(10) Patent No.: US 7,544,832 B2
(45) Date of Patent: Jun. 9, 2009

(54) REACTION COLUMN IN A SPECIAL COMBINATION WITH A NATURAL CIRCULATION EVAPORATOR

(75) Inventors: Jan Peter Bredehöft, Böhl-Iggelheim (DE); Hans-Jürgen Pallasch, Gönnheim (DE); Ludwig E. Heck, Edingen-Neckarhausen (DE); Eckhard Ströfer, Mannheim (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 563 days.

(21) Appl. No.: 10/503,005

(22) PCT Filed: Feb. 15, 2002

(86) PCT No.: PCT/EP02/01658
§ 371 (c)(1),
(2), (4) Date: Jul. 29, 2004

(87) PCT Pub. No.: WO03/068359
PCT Pub. Date: Aug. 21, 2003

(65) Prior Publication Data
US 2005/0020848 A1    Jan. 27, 2005

(51) Int. Cl.
*C07C 249/00* (2006.01)
(52) U.S. Cl. .................................................... 560/352
(58) Field of Classification Search ................. 560/330, 560/336, 352
See application file for complete search history.

(56) References Cited

U.S. PATENT DOCUMENTS

| 4,019,866 A | 4/1977 | Jaswal et al. |
| 4,118,286 A * | 10/1978 | Burns et al. .................... 203/89 |
| 4,380,615 A | 4/1983 | Sauerbrunn |
| 5,095,164 A | 3/1992 | Gabel et al. |

FOREIGN PATENT DOCUMENTS

| DE | 2 410 474 | 3/1974 |
| DE | 196 31 332 A1 | 5/1996 |
| DE | 100 27 779 A1 | 6/2000 |
| EP | A 0 302 336 | 2/1989 |

OTHER PUBLICATIONS

Perry's Chemical Engineers' Handbook (7th Edition), Edited by: Perry, R.H.; Green, D.W. © 1997 McGraw-Hill, p. 11-108.*
PUR, Nr. 7 3 Sufl. Hauser, p. 72, 1993.
Distillation Operation, McGraw-Hill, 1989, p. 97.

* cited by examiner

*Primary Examiner*—Karl J Puttlitz
(74) *Attorney, Agent, or Firm*—Fernando A. Borrego; Howard & Howard Attorneys PLLC

(57) ABSTRACT

An arrangement for carrying out chemical reactions comprises at least one distillation column and/or at least one container and at least one circulation evaporator, which are connected to one another via connecting elements, liquid being taken off completely or partly from a tray or from a stacked packing bed or from a dumped packing bed or from a liquid collector of the distillation column or being fed as an external feed stream below the lower tube sheet of the circulation evaporator to said evaporator.

11 Claims, 1 Drawing Sheet

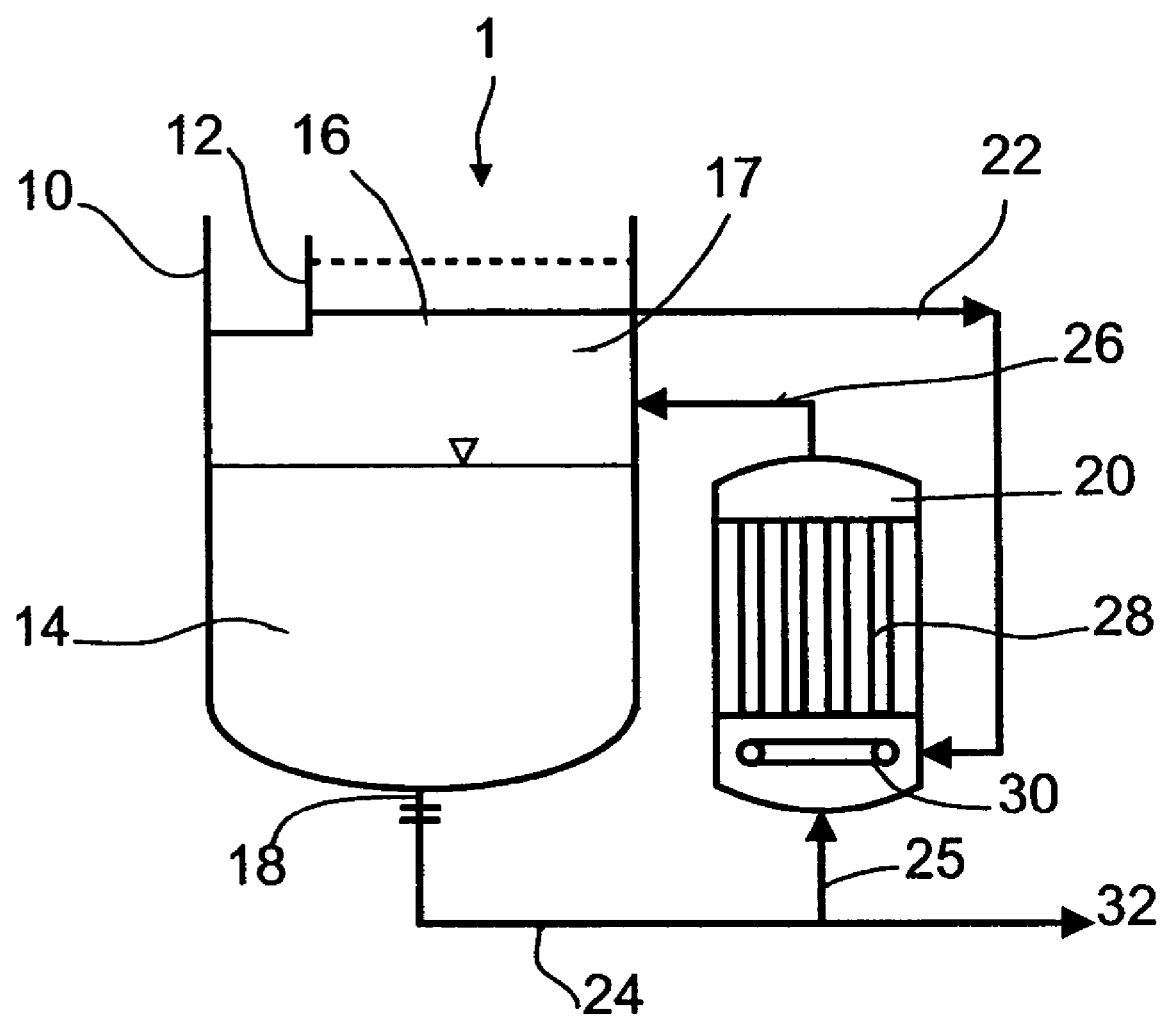

REACTION COLUMN IN A SPECIAL COMBINATION WITH A NATURAL CIRCULATION EVAPORATOR

The present invention relates to an arrangement for carrying out chemical reactions, comprising at least one distillation column and/or at least one container and at least one circulation evaporator, these being connected to one another by corresponding connecting elements.

Chemical reactions which are carried out using distillation columns are known, for example, from polyurethane chemistry. For example, a separation of the mononitration mixture, which is obtained in the preparation of tolylenediamine (TDA) by the nitration of toluene to be carried out in a first step to give a mixture of tolylenediamine isomers, can be achieved as a rule on an industrial scale only by a plurality of distillation steps.

Various mixing means which may also contain, inter alia, distillation means are also used in the synthesis of industrially important isocyanates, for example tolylene diisocyanate (TDI) or methylenediphenyl diisocyanate (MDI) via phosgenation.

Problems in syntheses of this type include the fact that, in the case of insufficient mixing of the specifically used reaction components and unfavorable reaction conditions, a smooth course of the reaction, i.e. optimum conversion in the reaction, which is decisive in particular for the magnitude of the yield, frequently cannot be achieved. The increased level of byproducts then obtained and unconverted starting materials, which also accumulate in the bottom of the reaction apparatus, have been separated off from the main product to date in a further expensive and time-consuming step and worked up (described in PUR-Kunststoffhandbuch No. 7, 3rd Edition, Hanser Verlag, page 77, Section 3.2.2).

A known arrangement for achieving an improved conversion in the reaction is an apparatus comprising a spatially divided bottom (hot/cold) within the reaction column used. With the aid of the divided bottom, it is possible to prevent the hot liquid which emerges from the evaporator connected to the reaction column from mixing again with the cold bottom content of the reaction column. As a result, on the one hand a hot bottom part, from which the bottom product is taken off for further working up, and, on the other hand, a cold bottom part are thus obtained. The cold liquid from the lowermost tray of the reaction column, which is present above the bottom, and that part of the hot bottom part which, owing to the spatial arrangement, overflows therefrom are mixed with the cold bottom part.

The low ratio of the volume of hot to cold bottom part may be regarded as a disadvantage of this arrangement. The attempts to date to overcome this disadvantage have however been unsuccessful because of the limits imposed, inter alia, by the design and size of the respective arrangement.

A further known arrangement attempts to solve this problem by increasing the size of the hot bottom part. In this arrangement, the spatial separation of cold and hot bottom part was dispensed with so that the cold bottom part is of course present below the hot bottom part. The liquid from the lowermost tray of the reaction column is fed directly in front of the connecting piece from which the bottom product can be taken off and which is present as a rule at the bottom of the column, i.e. in the cold bottom part.

However, the fact that, owing to the hot bottom part, the cold liquid already begins to evaporate during passage through the pipe conveying it, so that a liquid having gaseous components is passed in front of the connecting piece may be regarded as a disadvantage of this arrangement. These gaseous components in the liquid subsequently to be evaporated led to a deterioration in the circulation in the connected evaporator. This results as a rule in malfunctions or fouling. In this context, fouling is understood as meaning the formation of undesired deposits, for example on the respective inner surfaces of pipes, said formation occurring at relatively high temperatures.

Furthermore, Kister (Henry Kister, Distillation operation, MacGraw-Hill, 1989, page 97) describes the use of a once-through evaporator which is operated as a natural circulation evaporator for starting up a column. A combination of natural circulation evaporator and once-through evaporator is however not mentioned.

It is an object of the present invention to provide an arrangement by means of which chemical reactions, for example the TDI or MDI preparation described above, can be carried out economically without said disadvantages and with simultaneous improvement of the conversion in the reaction.

We have found that this object is achieved by an arrangement for carrying out chemical reactions, comprising at least one distillation column and/or at least one container and at least one circulation evaporator, which are connected to one another via connecting elements, wherein liquid is completely or partly fed from a tray or from a stacked packing bed or from a dumped packing bed or from a liquid collector of the distillation column or as an external feed stream below the lower tube sheet of the circulation evaporator to said evaporator.

The chemical reactions which can be carried out using this arrangement are preferably kinetically controlled reactions, endothermic equilibrium reactions or mass transfers, since the higher temperatures in these cases together with an identical liquid volume lead to faster and better conversions in the reactions.

However, the preparation of diisocyanates, in particular of TDI and MDI, is particularly preferably carried out.

The distillation column used is preferably a multistage continuous tray column.

Alternatively, tube columns, hold-up tray columns, falling-film columns, spray columns, bubble columns, columns containing dumped packings, columns containing stacked packings and hold-up packed columns, which are operated continuously, semibatchwise or batchwise, can also be used.

In vertical columns, for reasons relating to energy, in the majority of cases in principle the liquid phase flows from top to bottom and the gaseous phase from bottom to top. For the present invention, vertical columns whose phases can be fed countercurrently, in crossflow, cocurrently, cross-cocurrently and cross-countercurrently are preferably used, the respective form of the flow being determined by the internals.

In the context of the present invention, liquid is understood as meaning the condensate obtained in the distillation column and/or a liquid feed which is taken off from the lowermost of the trays provided in the distillation column. It is typical of a tray in a column that as a rule there is thermal equilibrium between the vapor ascending from a tray and the liquid flowing away from it. However, trays on which there is no thermodynamic equilibrium are also possible. In the case of the preferably used trays, a distinction should be made between trays with forced liquid transport and trays without forced liquid transport. Furthermore, the trays may be designed as exchange trays to increase the flexibility. Depending on the specified flow path, for example, cross-flow trays, deflected-flow trays or radial-flow trays may be used in the case of trays with forced liquid transport. A stacked packing bed or a dumped packing bed may also be provided instead of or in addition to these trays.

The dumped packing bed is preferably a more or less regularly arranged packing uniformly distributed over the entire height of the column and resting on a support grid. The beds consist of regularly shaped bodies, the sizes of the packings being very varied and being intended to realize a very large surface area and to provide the gas with a large free passage cross section. Preferably used types of packings are annular bodies, such as Raschig rings and Pall rings, and saddle elements, such as Intalox saddles and Berl saddles, which in turn may consist of various materials, for example ceramic, metal, glass and plastic.

In contrast to dumped packing beds having an irregular structure, stacked packings, also referred to as a whole as a stacked packing bed, constitute ordered column packings. The choice of the material of the stacked packings is determined mainly by the corrosion properties but also by flow parameters. The stacked packings may be different, for example in the form of unperforated plates and strips with and without surface structure (e.g. sieve plates, expanded metal) and may comprise woven, knitted and braded materials.

Furthermore, in the novel arrangement, the circulation evaporator is a natural circulation evaporator.

The evaporators used in the present invention may as a rule be any known evaporators. Preferably, however, forced-circulation evaporators, for example rising-film evaporators, centrifugal evaporators and rotary evaporators, and circulation evaporators, for example Robert evaporators, inclined evaporators and long-tube evaporators, and natural circulation evaporators are used. It is also possible to use falling-film evaporators, but the liquid would then have to be fed in above the tube sheet.

The particularly preferably provided once-through evaporator is an apparatus for evaporating the liquids, the liquid being completely or partly evaporated during a single passage through the apparatus.

The natural circulation evaporator defined is an evaporator which operates without the use of pumps, the fluid to be evaporated being heated up in the tubes of a tube bundle, generally by condensing steam, and being partly evaporated. A natural circulation arises as a result of the fluid density difference between the feed and tube bundle.

The connecting elements between distillation column and evaporator are preferably in the form of pipelines. Alternatively, baffle plates, shafts or hoses may also be used.

In a further preferred embodiment, the liquid is taken off from the feed of the distillation column or of the container and fed to the circulation evaporator below the lower tube sheet of said evaporator.

Furthermore, in a preferred embodiment of the arrangement according to the invention, the liquid fed to the circulation evaporator is mixed, preferably via at least one feed and/or distributor system below the lower tube sheet of the circulation evaporator, with a liquid circulating from the hot bottom part of the distillation column or of the container.

A preferably used feed and/or distributor system comprises dip tubes, direct feeds, tangential feeds, nozzle units or jet units.

Said system particularly preferably comprises an annular pipe below the lower tube sheet of the circulation evaporator or the use of static mixing elements in the case of the direct feed.

In a further preferred embodiment of the present invention, the distillation column or the container has a divided bottom, the divided bottom having at least one cold and at least one hot bottom part.

This division can be effected by dividing elements, for example a dividing wall, if a spatially cohesive bottom region is to be divided, or by spatial separation in such a way that the bottom parts are a distance apart so that mutual temperature influence is as far as possible prevented. The bottom can in principle be divided into more than two parts, the size of the individual bottom parts being freely determinable.

In a further embodiment of the present invention, when the novel arrangement is used for mixtures in which reactions take place, maximization of the hot and minimization of the cold bottom part are achieved with the same construction size.

In the context of the present invention, mixtures are both homogeneous and heterogeneous mixtures of one or more pure components. The homogeneous mixtures are preferably liquids. The heterogeneous mixtures are preferably one or more liquid phases, a gaseous phase and/or one or more solid phases.

The construction size is to be understood as meaning the construction size of the arrangement for carrying out a comparable conversion in the reaction. A smaller construction size would therefore mean a lower content of toxic or other hazardous substances.

In the form of the assembly, a novel arrangement has the advantage that the cold liquid evaporated on mixing with the hot liquid stabilizes the natural circulation and improves the heat transfer, thus counteracting fouling.

In addition to the avoidance of a two-phase flow in the bottom of the column, a lower inlet and outlet temperature and hence, at a specified heating medium temperature, a larger temperature difference in the evaporator are achieved in this combination as a result of the mixing of the two liquids.

The temperature of the discharge from the preferably used natural circulation evaporator preferably corresponds to the bottom temperature and is therefore identical to the evaporator outlet temperature in the once-through evaporator. The inlet temperature of the natural circulation evaporator is preferably between bottom temperature and discharge temperature and is determined by the resulting circulation rate.

The combination of natural circulation evaporator and once-through evaporator, in particular for the TDI process, leads to an improvement in the conversion in the reaction by maximizing the hot bottom part. Consequently, either the residence time for the phosgene can be decreased or the risk of fouling reduced or the conversion to the desired product TDI increased, this corresponding to a higher yield.

The use of the present invention in the case of kinetically controlled reactions, endothermic equilibrium reactions or mass transfers is particularly advantageous since the higher temperatures in these cases together with an identical liquid volume lead to faster and better conversions in the reaction.

Furthermore, according to the present invention, the process for the preparation of tolylene diisocyanate (TDI) from tolylenediamine (TDA) and its amine hydrochloride and phosgene can be carried out with the aid of the novel arrangement.

The process for the preparation of methylenediphenyl diisocyanate (MDT) from methylenediphenyldiamine (MDA) and its amine hydrochloride and phosgene can also be carried out with the aid of this arrangement.

According to the invention, the use of the arrangement for carrying out the process for the preparation of TDI or MDI is also envisaged.

The present invention is explained in more detail below for a preferred embodiment with reference to the attached drawing.

FIG. 1 shows a schematic diagram of a novel arrangement.

The arrangement 1 shown in FIG. 1 illustrates a preferred embodiment of the present invention. The arrangement 1 for carrying out the TDI process comprises a distillation column 10 having a lowermost tray 12 and a hot bottom part 14 and a discharge 16 for cold liquid, vapor space 17 and a discharge 18 for hot liquid, a natural circulation evaporator 20 and corresponding connecting pipelines 22 and 24 and a feed 25 and an outflow pipe 26 of the natural circulation evaporator 20 for connecting distillation column 10 and natural circulation evaporator 20.

The natural circulation evaporator 20 in turn comprises an evaporator tube bundle 28, a distributor ring 30 and the feed 25 and the outflow pipe 26.

During the TDI process, liquid from the hot bottom part 14 of the distillation column 10 is fed through the discharge 18, the connecting pipeline 24 and the feed 25 to the distributor ring 30. At the same time, the liquid collected on the lowermost tray 12 of the distillation column 10 is removed from the distillation column 10 via the discharge 16 and fed via the connecting pipeline 22 likewise to the distributor ring 30 of the natural circulation evaporator 20.

These two liquids fed to the distributor ring 30 of the natural circulation evaporator 20 are preferably mixed in the distributor ring 30. The cold liquid evaporates and thus stabilizes the natural circulation and simultaneously improves the heat transfer.

The actual evaporation process in the natural circulation evaporator 20 takes place through heating of the evaporator tube bundle 28, the liquid fed into the individual tubes of the evaporator tube bundle 28 from the distributor ring 30 being heated. If the wall temperature of the tubes is sufficiently high, the liquid begins to boil in the tubes of the evaporator tube bundle 28 by bubbles initially forming on the tube wall. They become detached and, owing to the buoyancy, rise to the upper tube end to enter the vapor space 17 as vapor via the outflow pipe 26. As a result of the formation of vapor bubbles, the mean density in the individual tubes of the evaporator tube bundle 28 decreases, so that the hydrostatic pressure in the tubes is lower than that in the hot bottom part 14 of the distillation column 10. This difference in hydrostatic pressure causes a liquid flow from the hot bottom part 14 of the distillation column 10 to the evaporator tube bundle 28 of the natural circulation evaporator 20, in order to compensate the pressure difference. The liquid flow from the hot bottom part 14 of the distillation column 10 to the evaporator tube bundle 28 of the natural circulation evaporator 20 raises the two-phase mixture in the individual evaporator tubes beyond the upper tube sheet into the vapor space 17, the vapor bubbles formed entraining portions of liquid. These droplets are separated from the vapor space 17 by gravitational force or a suitable separator and fall back into the hot bottom part 14 of the distillation column 10. An automatic circulation flow thus arises.

The discharge 32 serves as a bottom take-off. Through it, the bottom product can be taken off under flow rate control in order, for example, to be further treated or worked up in a downstream reactor.

We claim:

1. A method for preparation of diisocyanates with at least one distillation column and/or at least one vessel and at least one circulation evaporator, wherein the distillation column and/or the vessel are connected to the circulation evaporator via connecting elements which feed liquid from a bottom part of the distillation column and/or the vessel to the circulation evaporator below a lower tube sheet of the circulation evaporator, said method further comprises completely or partly feeding liquid (i) from a tray or from a stacked packing bed or from a dumped packing bed or from a liquid collector of the distillation column to the circulation evaporator below a lower tube sheet of the circulation evaporator, or (ii) as a feed stream external to the distillation column and/or the vessel to the circulation evaporator below a lower tube sheet of the circulation evaporator.

2. A method as claimed in claim 1, wherein the circulation evaporator is a natural circulation evaporator.

3. A method as claimed in claim 1, wherein the liquid is taken off from the feed of the distillation column or of the vessel and is fed to the circulation evaporator below the lower tube sheet of the circulation evaporator.

4. A method as claimed in claim 1, wherein the distillation column or the vessel has a divided bottom.

5. A method as claimed in claim 4, wherein the divided bottom has at least one cold and at least one hot bottom part.

6. A method as claimed in claim 5, wherein a size of the hot bottom part of the divided bottom is equal to a size of the cold bottom part of the divided bottom.

7. A method as claimed in claim 1, wherein the liquid fed to the circulation evaporator via (i) or (ii) is mixed below the lower tube sheet of the circulation evaporator with the liquid circulating from the hot bottom part of the distillation column and/or of the vessel.

8. A method as claimed in claim 1, wherein the diisocyanate is tolylene diisocyanate (TDI).

9. A method as claimed in claim 1, wherein the diisocyanate is methylenediphenyl diisocyanate (MDI).

10. A method as claimed in claim 7, wherein the liquid fed to the circulation evaporator via (i) or (ii) is mixed with the liquid circulating from the hot bottom part of the distillation column and/or of the vessel via at least one distributor system.

11. A method as claimed in claim 7, wherein the liquid fed to the circulation evaporator via (i) or (ii) is cold relative to the liquid feed from the bottom part of the distillation column and/or the vessel.

* * * * *